(12) United States Patent
Haldeman et al.

(10) Patent No.: US 6,970,748 B2
(45) Date of Patent: Nov. 29, 2005

(54) METHOD OF USING FINISHING WIRE WITH LARGE BALL-NOSE TIP

(75) Inventors: Paul Craig Haldeman, Murrieta, CA (US); Michael D. Whitt, Temecula, CA (US); James Robert Niederecker, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 348 days.

(21) Appl. No.: 10/116,741

(22) Filed: Apr. 4, 2002

(65) Prior Publication Data

US 2003/0191515 A1 Oct. 9, 2003

(51) Int. Cl.[7] .............................................. A61N 1/05
(52) U.S. Cl. .................................................. 607/122
(58) Field of Search ................................. 607/122, 119, 607/126–128, 120; 600/585; 606/129; 601/126.48

(56) References Cited

U.S. PATENT DOCUMENTS

| | | | | |
|---|---|---|---|---|
| 5,129,404 A | | 7/1992 | Spher et al. | |
| 5,344,439 A | * | 9/1994 | Otten | 607/126 |
| 6,219,582 B1 | * | 4/2001 | Hofstad et al. | 607/122 |
| 6,223,087 B1 | * | 4/2001 | Williams | 607/119 |
| 6,356,791 B1 | * | 3/2002 | Westlund et al. | 607/115 |
| 6,456,890 B2 | * | 9/2002 | Pianca et al. | 607/122 |
| 6,466,811 B1 | * | 10/2002 | Hassett | 600/374 |

* cited by examiner

*Primary Examiner*—Jeffrey R. Jastrzab
*Assistant Examiner*—Roderick Bradford

(74) *Attorney, Agent, or Firm*—Hollingsworth & Funk, LLC

(57) ABSTRACT

A finishing wire with a ball nose tip is used to secure an implantable device such as a cardiac pacing lead during implantation procedures. The finishing wire includes a proximal shaft, and a ball-nosed distal end. The ball-nosed distal end of the finishing wire is sized to interface with an implantable device having a narrowed distal tip. The length of the finishing wire is greater than the length of the implantable device.

36 Claims, 3 Drawing Sheets

U.S. 6,970,748 B2

METHOD OF USING FINISHING WIRE WITH LARGE BALL-NOSE TIP

FIELD OF THE INVENTION

The invention relates generally to methods of using finishing wires, and more particularly to method of using finishing wires involving securing of leads during cardiac pacing lead implantation procedures.

BACKGROUND OF THE INVENTION

Implantable cardioverter/defibrillators (ICDs) are well known and effective devices for treating patients with cardiac rhythmic dysfunction. The ICD has a pulse generator and an electrical lead with an electrode at the tip. The ICD implantation procedure generally takes about two hours and is relatively low risk, as it rarely requires open heart surgery. Usually, one to two lead wires are placed through a large vein in the chest and threaded down to the inside of the heart. The lead wires are then connected to the pulse generator, which is placed in a pocket under the skin of the patient.

The details of the implantation procedure vary depending of the condition and anatomy of the patient, but typically a guiding catheter is introduced through a major blood vessel such as the cephalic vein. The catheter is then moved through the vasculature to locate an access vessel of interest in the heart, such as the coronary sinus ostium. The catheter can either be navigated on its own through the venous pathway to the ostium or be slid over a previously inserted guide wire. After the coronary sinus ostium has been located by the guiding catheter, an ICD lead can be inserted through the catheter into the coronary sinus or one of its branches.

There is a need for a technique of temporarily securing a newly implanted lead during the time in which a guiding apparatus used in the implantation procedure is removed, such that implantation time and patient trauma are reduced. The present invention fulfills this and other needs, and addresses other deficiencies of prior art implementations and techniques.

SUMMARY OF THE INVENTION

The present invention is directed to methods of using a finishing wire for securing an implantable cardiac device during implantation procedures According to one embodiment of the invention, a finishing wire for use during implantable cardiac lead implantation includes a proximal shaft and a ball-nosed distal end. The ball-nosed distal end is connected to a distal end of the proximal shaft. The ball nosed distal end has a diameter larger than a diameter of the proximal shaft. The ball-nosed distal end is sized to interfere with the narrowed distal end of the implantable cardiac lead during lead implantation. A combined length of the proximal shaft and ball-nosed distal end is typically greater than a length of the implantable cardiac lead.

In one configuration, the ball-nosed distal end includes a substantially hemispherical tip, whereby the substantially hemispherical tip interferes with the narrowed distal end of the implantable cardiac lead. The diameter of the ball-nosed distal end in this configuration can be about twice the diameter of the proximal shaft. In another useful arrangement, the diameter of the ball-nosed distal end ranges from about 0.015 inches to about 0.030 inches. Further, the diameter of the proximal shaft can range from about 0.010 inches to about 0.020 inches, and a length of the finishing wire can range from about 55 inches to about 65 inches.

In another configuration, the ball nosed distal end includes a tapered section, a necked section, and a distal tip. The tapered section includes a proximal end connected to the distal end of the proximal shaft. The tapered section also includes a proximal diameter about equal to the diameter of the proximal shaft. A distal diameter of the tapered section is less than the proximal diameter of the tapered section. The necked section has a proximal end connected to a distal end of the tapered section. The proximal end of the necked section has a substantially constant diameter. The necked section further includes a proximal diameter about equal to the distal diameter of the tapered section, a distal diameter, and a distal end including a taper. The distal diameter of the necked section is greater than the proximal diameter of the necked section. The distal tip has a proximal end connected to the distal end of the necked section. The distal tip has a diameter that is about equal to the distal diameter of the necked section. The distal tip further includes a substantially hemispherical distal end. The substantially hemispherical distal end of the distal tip interferes with the narrowed distal end of the implantable cardiac lead.

In one particular configuration of a finishing wire for use in lead implantation procedures, the distal diameter of the necked section is about 3 times the proximal diameter of the necked section, and the diameter of the proximal shaft is about 1.5 times the proximal diameter of the necked section. In yet another configuration, the diameter of the distal tip is about twice the diameter of the proximal shaft.

In accordance with the principles of the present invention, a method for inserting a payload into a destination vessel of a patient's heart involves providing a payload having a narrowed distal end and providing a guide catheter for longitudinally guiding the payload. The method further involves providing a finishing wire including a proximal shaft and a ball-nosed distal end connected to a distal end of the proximal shaft. The ball-nosed distal end has a diameter larger than a diameter of the proximal shaft and the ball-nosed distal end is sized to interfere with the narrowed distal end of the payload. A combined length of the proximal shaft and ball-nosed distal end is greater than a length of the implantable cardiac lead.

The method according to the present invention further involves inserting the guiding catheter into a chamber of the patient's heart via an access vessel. Then the payload is inserted through the guide catheter into a destination vessel of the patient's heart to seat the payload into a branch of the destination vessel. The finishing wire is inserted through the payload such that the distal tip of the finishing wire contacts the narrowed distal end of the payload. The method then involves fixing a proximal end of the finishing wire to secure the payload against dislodgment.

In another embodiment of the method according to the present invention, a guide wire is also provided for longitudinally guiding the payload. The guide wire is inserted through the guide catheter into the destination vessel of the patient's heart after inserting the guiding catheter into a chamber of the patient's heart. This embodiment of the method further involves removing the guide wire from the guide catheter after seating the payload into a branch of the destination vessel.

In one aspect of the previously described methods, the chamber of the patient's heart includes the right atrium, the destination vessel includes the coronary sinus, and the patient's access vessel includes the superior vena cava. In another aspect of the methods, the payload comprises an implantable cardiac pacing lead.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
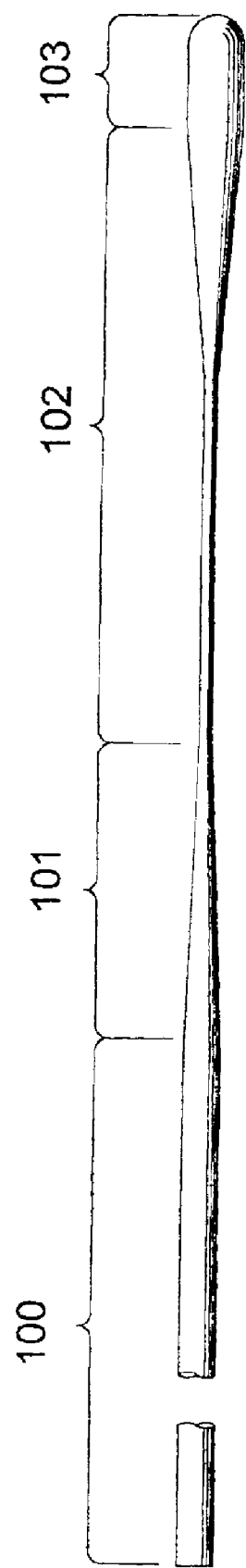
FIG. 1 is an external view of a finishing wire particularly well suited for use when inserting a payload into a destination vessel of a patient's heart according to one embodiment of the invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

The present invention is directed to methods of using a uniquely shaped finishing wire. The present invention is particularly useful during catheter removal after implantation of an implantable cardiac device, such as a pacing lead. A finishing wire methodology of the present invention employs a finishing wire having a unique tip shape that is optimized for this task.

For procedures that use an over-the-wire type of lead, a small diameter guide wire is located within the guide catheter, and the lead is advanced through the catheter and over the guide wire. The lead is seated in a tributary of the coronary sinus, for example, at which point the guide wire, if used, can be withdrawn. Electrical testing of the implanted pacing lead is performed to ensure it is successfully positioned, and the lead may be repositioned or replaced if testing indicates a problem.

Once the lead has been successfully positioned, it is necessary to remove any guide wires and the guide catheter. However, catheter removal can disturb or dislodge the pacing lead, as can other movements on the proximal end of the lead until the lead is stabilized. A method of using a finishing wire in accordance with the present invention ensures that such adverse disturbance or dislodgment of the pacing lead during catheter removal does not occur.

Turning now to FIG. 1, various sections of a finishing wire for use when inserting a payload into a destination vessel of a patient's heart are illustrated. The finishing wire includes a proximal shaft 100 and a ball-nosed distal end. In one configuration, the ball-nosed distal end of the finishing wire can include a tapered section 101, a necked section 102, and a distal tip 103. The finishing wire is typically made from 304V stainless steel, although other materials may be appropriate. The ball-nosed distal end shape may be formed by various methods known in the art, however methods that allow one-piece construction, such as swaging or grinding, are ideal. The distal tip may be micro-finished by procedures known in the art, such as electropolishing. All transitions in the tip profile are preferably smooth and continuous.

Figure 2:
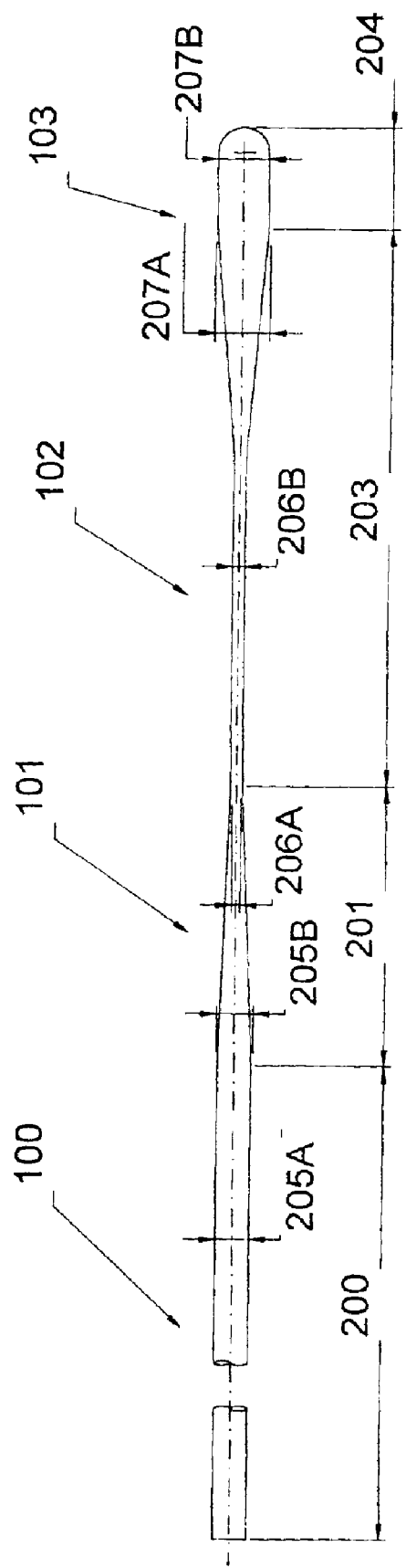
FIG. 2 is an external view of the finishing wire from FIG. 1 showing sectional measurements.

In FIG. 2, the dimensions of various finishing wire features are indicated. In one useful configuration, the overall length of the finishing wire may range from about 55 inches to about 65 inches. The proximal shaft 100 takes up the substantial length of the finishing wire, the proximal shaft 100 having a length 200 ranging from about 50 to about 60 inches in one arrangement. The proximal shaft 100 has a diameter 205A ranging from about 0.010 to about 0.020 inches.

The tapered section 101 interfaces with the proximal shaft 100, and a proximal diameter 205B of the tapered section 101 is substantially equal to the proximal shaft diameter 205A. A distal diameter 206A of the tapered section 101 is smaller than the proximal diameter 205B. In one configuration, the distal diameter 206A of the tapered section 101 ranges from 0.003 to 0.009 inches. The tapered section 101 has a length 201 ranging from about 2 inches to about 5 inches.

The necked section 102 interfaces with the tapered section 101. The proximal end of the necked section 102 has a section with substantially constant diameter 206B. The diameter 206B is substantially equal to the distal diameter 206A of the tapered section 101. In a particularly useful arrangement, the length of the proximal diameter part of the necked section 102 ranges between 0.50 and 1.25 inches. The necked section 102 tapers to a larger diameter 207A at the distal end, the diameter 207A ranging from about 0.015 to about 0.030 inches. The length of the distal end of the necked section 102 ranges from about 0.05 inches to about 0.25 inches.

The distal tip 103 interfaces with the distal end of the necked section 102, and has a diameter 207B substantially equal to the necked section distal diameter 207A. The distal end of the distal tip 103 is substantially hemispherical, with the spherical diameter being substantially equal to the distal tip diameter 207B. The length 204 of the distal tip 103 ranges from about 0.010 to about 0.100 inches.

In another configuration, the distal diameter 207A of the necked section 102 is about 3 times the proximal diameter 206B of the necked section 102. In this configuration, the diameter 205A of the proximal shaft 100 is about 1.5 times the proximal diameter 206B of the necked section 102.

Figure 3:
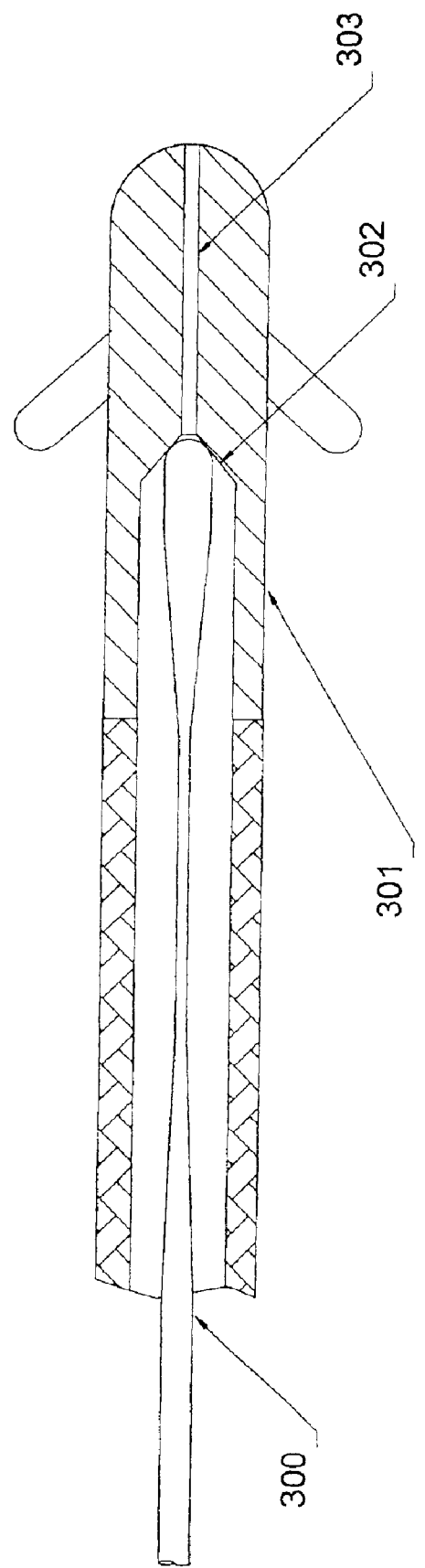
FIG. 3 is a cutaway view of a pacing lead showing the distal end of a uniquely shaped finishing wire interfacing with the pacing lead during a lead implantation procedure.

The distal tip 103 is designed such that it will positively interfere with an implantable device having a narrowed distal tip during a lead implantation procedure of the present invention. This interfering arrangement is illustrated in FIG. 3, which is a cutaway view of an implantable pacing lead 301. The pacing lead 301 has a chamfer 302 at a distal tip. When a finishing wire 300 is advanced to the chamfer 302, the chamfer 302 interfaces with the finishing wire 300, allowing the finishing wire 300 to exert a holding force on the pacing lead 301. In a configuration suitable for over-the-wire pacing leads, the pacing lead 301 includes an opening 303 through the center of the chamfer 302 that allows the lead 301 to be advanced over a small guide wire.

A finishing wire according to the present invention can be effectively used during implantation of cardiac devices, in particular pacing and defibrillation leads. In such a procedure, a guide catheter is introduced into the heart. The guide catheter cannulates a destination vessel, typically the coronary sinus. A guide wire can be inserted through the guide catheter and distally advanced beyond a distal end of the guide catheter. The guide wire can be seated in a branch of the destination vessel. A lead 301, such as shown in FIG. 3, can be advanced through the guide catheter and over the guide wire. The lead 301 is seated into the branch of the destination vessel.

After the lead 301 is seated, the guide wire may be removed. Before removing the guide catheter, the finishing wire 300 can be inserted into the lead 301. The unique tip shape of the finishing wire 300 allows it to be easily advanced through the lead 301 until the finishing wire 300 interfaces with the distal end of the lead 301. The finishing wire 300 can then be fixed at a proximal end to assist in securing the lead 301 against dislodgment during guide catheter removal. The finishing wire 300 can be left in place to further secure the lead 301 against any other disruptions during the procedure that might dislodge the lead.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of inserting a payload into a destination vessel of a patient's heart, comprising:
   providing a payload having a narrowed distal end;
   providing a guide catheter for longitudinally guiding the payload;
   providing a finishing wire, comprising:
      a proximal shaft having a diameter; and
      a ball-nosed distal end connected to a distal end of the proximal shaft, the ball nosed distal end having a diameter larger than the diameter of at least a portion of the proximal shaft, the ball-nosed distal end sized to interfere with the narrowed distal end of the payload, and a combined length of the proximal shaft and ball-nosed distal end being greater than a length of the payload;
   inserting the guiding catheter into a chamber of the patient's heart via an access vessel;
   inserting the payload through the guide catheter into the destination vessel of the patient's heart to seat the payload in the destination vessel;
   inserting the finishing wire through the payload such that the ball-nosed distal end of the finishing wire contacts the narrowed distal end of the payload; and
   fixing, while the ball-nosed distal end of the finishing wire is in contact with the narrowed distal end of the payload, a proximal end of the finishing wire to secure the payload against dislodgment.

2. A method according to claim 1, wherein the chamber of the patient's heart includes the right atrium.

3. A method according to claim 1, wherein the destination vessel includes the coronary sinus.

4. A method according to claim 1, wherein the patient's access vessel includes the superior vena cava.

5. A method according to claim 1, wherein the payload comprises an implantable cardiac pacing lead.

6. A method according to claim 1, wherein the ball-nosed distal end comprises a substantially hemispherical tip, whereby the substantially hemispherical tip is sized to interfere with the narrowed distal end of the payload.

7. A method according to claim 1, wherein the diameter of the ball-nosed distal end is about twice the diameter of the proximal shaft.

8. A method according to claim 1, wherein the diameter of the ball-nosed distal end ranges from about 0.015 inches to about 0.030 inches.

9. A method according to claim 1, wherein the diameter of the proximal shaft ranges from about 0.010 inches to about 0.020 inches.

10. A method according to claim 1, wherein a length of the finishing wire ranges from about 55 inches to about 65 inches.

11. A method according to claim 1, wherein the ball nosed distal end comprises:
   a tapered section comprising a proximal end connected to the distal end of the proximal shaft, a proximal diameter about equal to the diameter of the proximal shaft, and a distal diameter less than the proximal diameter;
   a necked section comprising a proximal end connected to a distal end of the tapered section and having a substantially constant diameter, the necked section further comprising a proximal diameter about equal to the distal diameter of the tapered section and a distal end comprising a taper such that the distal diameter is greater than the proximal diameter; and
   a distal tip comprising a proximal end connected to a distal end of the necked section, the distal tip having a diameter about equal to the distal diameter of the necked section, the distal tip further comprising a substantially hemispherical distal end, whereby the substantially hemispherical distal end of the distal tip is sized to interfere with the narrowed distal end of the payload.

12. A method according to claim 11, wherein the distal diameter of the necked section is about 3 times the proximal diameter of the necked section and the diameter of the proximal shaft is about 1.5 times the proximal diameter of the necked section.

13. A method according to claim 11, wherein the diameter of the proximal shaft ranges from about 0.010 inches to about 0.020 inches and the length of the proximal shaft ranges from about 50 inches to about 60 inches.

14. A method according to claim 11, wherein the proximal diameter of the tapered section ranges from about 0.010 inches to about 0.020 inches, the distal diameter of the tapered section ranges from about 0.003 inches to about 0.009 inches, and a length of the tapered section ranges from about 2 inches to about 5 inches.

15. A method according to claim 11, wherein the proximal diameter of the necked section ranges from about 0.003 inches to about 0.009 inches, the distal diameter of the necked section ranges from about 0.015 inches to about 0.030 inches, a length of the distal end of the necked section ranges from about 0.05 inches to about 0.25 inches, and a length of the proximal end of the necked section ranges from about 0.50 inches to about 1.25 inches.

16. A method according to claim 11, wherein the diameter of the distal tip ranges from about 0.015 inches to about 0.030 inches and a length of the distal tip ranges from about 0.010 inches to about 0.100 inches.

17. A method according to claim 11, wherein the diameter of the distal tip is about twice the diameter of the proximal shaft.

18. A method of inserting a payload into a destination vessel of a patient's heart, comprising:
  providing a payload having a narrowed distal end;
  providing a guide catheter for longitudinally guiding the payload;
  providing a guide wire for longitudinally guiding the payload;
  providing a finishing wire, comprising:
    a proximal shaft comprising a diameter; and
    a ball-nosed distal end connected to a distal end of the proximal shaft, the ball nosed distal end having a diameter larger than at least a portion of a diameter of the proximal shaft, the ball-nosed distal end sized to interfere with the narrowed distal end of the payload, and a combined length of the proximal shaft and ball-nosed distal end greater than a length of the payload;
  inserting the guiding catheter into a chamber of the patient's heart via an access vessel;
  inserting the guide wire through the guide catheter into the destination vessel of the patient's heart;
  inserting the payload through the guide catheter and over the guide wire into a destination vessel of the patient's heart to seat the payload in the destination vessel;
  removing the guide wire from the guide catheter;
  inserting the finishing wire through the payload such that the ball-nosed distal end of the finishing wire contacts the narrowed distal end of the payload; and
  fixing, while the ball-nosed distal end of the finishing wire is in contact with the narrowed distal end of the payload, a proximal end of the finishing wire to secure the payload against dislodgment.

19. A method according to claim 18, wherein the chamber of the patient's heart includes the right atrium.

20. A method according to claim 18, wherein the destination vessel includes the coronary sinus.

21. A method according to claim 18, wherein the patient's access vessel includes the superior vena cava.

22. A method according to claim 18, wherein the payload comprises an implantable cardiac pacing lead.

23. A method according to claim 18, wherein the ball-nosed distal end comprises a substantially hemispherical tip, whereby the substantially hemispherical tip is sized to interfere with the narrowed distal end of the payload.

24. A method according to claim 18, wherein the diameter of the ball-nosed distal end is about twice the diameter of the proximal shaft.

25. A method according to claim 18, wherein the diameter of the ball-nosed distal end ranges from about 0.015 inches to about 0.030 inches.

26. A method according to claim 18, wherein the diameter of the proximal shaft ranges from about 0.010 inches to about 0.020 inches.

27. A method according to claim 18, wherein a length of the finishing wire ranges from about 55 inches to about 65 inches.

28. A method according to claim 18, wherein the ball nosed distal end comprises:
  a tapered section comprising a proximal end connected to the distal end of the proximal shaft, a proximal diameter about equal to the diameter of the proximal shaft, and a distal diameter less than the proximal diameter;
  a necked section comprising a proximal end connected to a distal end of the tapered section and having a substantially constant diameter, the necked section further comprising a proximal diameter about equal to the distal diameter of the tapered section and a distal end comprising a taper such that the distal diameter is greater than the proximal diameter; and
  a distal tip comprising a proximal end connected to a distal end of the necked section, the distal tip having a diameter about equal to the distal diameter of the necked section, the distal tip further comprising a substantially hemispherical distal end, whereby the substantially hemispherical distal end of the distal tip is sized to interfere with the narrowed distal end of the payload.

29. A method according to claim 28, wherein the distal diameter of the necked section is about 3 times the proximal diameter of the necked section and the diameter of the proximal shaft is about 1.5 times the proximal diameter of the necked section.

30. A method according to claim 28, wherein the diameter of the proximal shaft ranges from about 0.010 inches to about 0.020 inches and the length of the proximal shaft ranges from about 50 inches to about 60 inches.

31. A method according to claim 28, wherein the proximal diameter of the tapered section ranges from about 0.010 inches to about 0.020 inches, the distal diameter of the tapered section ranges from about 0.003 inches to about 0.009 inches, and a length of the tapered section ranges from about 2 inches to about 5 inches.

32. A method according to claim 28, wherein the proximal diameter of the necked section ranges from about 0.003 inches to about 0.009 inches, the distal diameter of the necked section ranges from about 0.015 inches to about 0.030 inches, a length of the distal end of the necked section ranges from about 0.05 inches to about 0.25 inches, and a length of the proximal end of the necked section ranges from about 0.50 inches to about 1.25 inches.

33. A method according to claim 28, wherein the diameter of the distal tip ranges from about 0.015 inches to about 0.030 inches and a length of the distal tip ranges from about 0.010 inches to about 0.100 inches.

34. A method according to claim 28, wherein the diameter of the distal tip is about twice the diameter of the proximal shaft.

35. A method according to claim 1, further comprising:
  proximally advancing the guide cathether while the finishing wire secures the payload against dislodgment to remove the guide catheter from the patient's body; and
  proximally advancing the finishing wire relative to the payload to remove the finishing wire from the patient's body.

36. A method according to claim 28, further comprising:
  proximally advancing the guide cathether while the finishing wire secures the payload against dislodgment to remove the guide catheter from the patient's body; and
  proximally advancing the finishing wire relative to the payload to remove the finishing wire from the patient's body.

* * * * *

UNITED STATES PATENT AND TRADEMARK OFFICE
CERTIFICATE OF CORRECTION

PATENT NO. : 6,970,748 B2 Page 1 of 1
APPLICATION NO. : 10/116741
DATED : November 29, 2005
INVENTOR(S) : Haldeman et al.

It is certified that error appears in the above-identified patent and that said Letters Patent is hereby corrected as shown below:

<u>In the Specification</u>

Col. 1, line 7: "to method of" should read --to methods of--.

Col. 1, line 46: "procedures According" should read --procedures. According--.

Col. 4, line 35: "the length of the" should read --the length 203 of the--.

<u>In the Claims</u>

Col. 8, line 49: "the guide cathether" should read --the guide catheter--.

Col. 8, line 57: "the guide cathether" should read --the guide catheter--.

Signed and Sealed this

Eighteenth Day of March, 2008

JON W. DUDAS
*Director of the United States Patent and Trademark Office*